US008419810B2

(12) United States Patent
Hillion et al.

(10) Patent No.: US 8,419,810 B2
(45) Date of Patent: *Apr. 16, 2013

(54) METHOD FOR PRODUCING BIOFUELS, TRANSFORMING TRIGLYCERIDES INTO AT LEAST TWO BIOFUEL FAMILIES: FATTY ACID MONOESTERS AND ETHERS AND/OR SOLUBLE GLYCEROL ACETALS

(75) Inventors: Gerard Hillion, Herblay (FR); Bruno Delfort, Paris (FR); Isabelle Durand, Rueil Malmaison (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 804 days.

This patent is subject to a terminal disclaimer.

(21) Appl. No.: 10/590,351

(22) PCT Filed: Jan. 27, 2005

(86) PCT No.: PCT/FR2005/000185
§ 371 (c)(1),
(2), (4) Date: Jun. 20, 2007

(87) PCT Pub. No.: WO2005/093015
PCT Pub. Date: Oct. 6, 2005

(65) Prior Publication Data
US 2007/0283619 A1 Dec. 13, 2007

(30) Foreign Application Priority Data

Feb. 24, 2004 (FR) ..................... 04 01918
Feb. 24, 2004 (FR) ..................... 04 01919

(51) Int. Cl.
*C10L 1/19* (2006.01)
(52) U.S. Cl.
USPC ............................. 44/388; 44/308
(58) Field of Classification Search ......... 44/388
See application file for complete search history.

(56) References Cited

U.S. PATENT DOCUMENTS

| 5,578,090 | A | * | 11/1996 | Bradin | 44/308 |
| 5,908,946 | A | | 6/1999 | Stern et al. | |
| 6,174,501 | B1 | | 1/2001 | Noureddini | |
| 6,878,837 | B2 | * | 4/2005 | Bournay et al. | 554/169 |
| 6,887,283 | B1 | * | 5/2005 | Ginosar et al. | 44/388 |
| 2003/0167681 | A1 | * | 9/2003 | Delgado Puche | 44/388 |

FOREIGN PATENT DOCUMENTS

| EP | 1331260 A | 7/2003 |
| FR | 2 752 242 | 2/1998 |
| FR | 2794768 A | 12/2000 |
| FR | 2794768 A1 | * 12/2000 |
| FR | 2855517 A1 | * 12/2004 |
| FR | 2855519 A1 | * 12/2004 |

OTHER PUBLICATIONS

English Translation of FR2794768A1.*
English Abstract of FR 285519 A1.*
English Translation of FR 2794768a1.*
Wessendorf R: "Glycerinderivate ALS Kraftstoffkomponenten" Erdoel Erdgas Kohle, Urban, Hamburg, Wien, DE, vol. 48, No. 3, Mar. 1, 1995, pp. 138-143, XP000501434 ISSN: 0179-3187 le document en entier.

* cited by examiner

*Primary Examiner* — Ellen McAvoy
*Assistant Examiner* — Ming Cheung Po
(74) *Attorney, Agent, or Firm* — Millen, White, Zelano & Branigan, P.C.

(57) ABSTRACT

A process for producing biofuels by transforming triglycerides into at least two families of biofuels, monoesters of fatty acids and soluble ethers and/or acetals of glycerol, comprises:

at least one transesterification step in which said triglyceride is reacted by heterogeneous catalysis with at least one primary monoalcohol selected from methanol and ethanol to produce at least one methyl and/or ethyl ester of the fatty acids of the starting triglycerides and glycerol, said products being free of by-products; and an etherification step in which the glycerol is reacted with at least one olefinic hydrocarbon containing 4 to 12 carbon atoms; and/or an acetalization step in which the glycerol is reacted with at least one compound selected from aldehydes, ketones and acetals derived from aldehydes or ketones.

17 Claims, No Drawings

METHOD FOR PRODUCING BIOFUELS, TRANSFORMING TRIGLYCERIDES INTO AT LEAST TWO BIOFUEL FAMILIES: FATTY ACID MONOESTERS AND ETHERS AND/OR SOLUBLE GLYCEROL ACETALS

The invention relates to a process for producing biofuels from triglycerides, resulting in a mixture of monoesters of fatty acids and soluble glycerol derivatives, namely ethers and/or acetals of glycerol.

The term "biofuels" means fuels or fuel constituents constituted by (or comprising) one or more products, in particular oxygen-containing products of natural origin. More particularly, the term "biodiesel" means a fuel or a fuel constituent for diesel engines constituted by (or comprising) at least one alkyl ester of a fatty acid of natural origin, such as a mixture of methyl esters of vegetable oils (rapeseed, sunflower, etc).

The massive envisageable increase in demand for biodiesel will result in the production of a quantity of glycerol equivalent to about 10% by weight of the biodiesel produced. As an example, an increase in the production of biodiesel of 1 million tonnes/year in Europe would cause an associated production of about 100000 t/yr of glycerol, i.e. about 50% of the market for glycerol in Europe. Known application sectors for glycerol are not sufficient to absorb such quantities, and so it would be appropriate to investigate novel applications where such over-production can be used. Because of the envisaged quantities of glycerol, such an application could only concern large tonnages.

One solution to this problem consists of using glycerol as the fuel base. Since glycerol is intrinsically insoluble in hydrocarbons, it is necessary to convert it into one (or more) products which are soluble in the fuel(s).

Known pathways for obtaining compounds which are soluble in hydrocarbons which may be cited include the transformation of glycerol into ethers, in particular into a mixture of mono-, di- and tri-tertiobutyl ethers. This operation is carried out by reacting glycerol with isobutene, generally in the presence of an acid catalyst, using various procedures which are well known to the skilled person (see, for example, U.S. Pat. No. 1,968,033). The preparation in this way of compositions which are soluble in hydrocarbons (see, for example, U.S. Pat. Nos. 2,841,479, 2,184,956, 5,476,971 and 5,731,476) is known.

The transformation of glycerol into an acetal of glycerol can also be cited. This operation may be carried out by reacting glycerol with an aldehyde or a ketone, generally in the presence of an acid catalyst using various procedures which are well known to the skilled person. The preparation in this way of compositions which are soluble in hydrocarbons, as described by the same Applicant in French patent FR-B-2 833 607, is known.

In these two cases, the chemistry involved necessitates the use of a glycerol which satisfies certain requirements as regards quality and purity. It is imperative that the glycerol should be neutral, that it should contain no salt or mineral or metallic compound, and that its water content should be very low.

However, the crude glycerol obtained from conventional processes for producing biodiesel does not satisfy those requirements. Conventional processes for producing biodiesel uses homogeneous generally basic catalysts, for example sodium hydroxide, potassium hydroxide, or sodium or potassium alcoholates such as sodium methylate. Said catalysts, after the transesterification of the triglyceride into methyl ester by methanol, for example, are found both in the ester, generally in the form of metal soaps/carboxylates, for example of sodium, and also in the co-produced glycerol in the form of an alcoholate, for example of sodium or potassium. In all cases, when the transesterification reaction is catalyzed by a homogeneous catalyst, the glycerol obtained contains catalyst or, usually, a compound from the catalyst, for example sodium or potassium glycerate. In many cases, the glycerol also contains water in proportions which can be from a few % to 35%, for example, depending on the process used.

The crude glycerol obtained from conventional processes for producing biodiesel cannot be used directly for the modification by an olefin such as isobutene to produce mixtures of ethers as this reaction demands a neutral glycerol which is thus free of alcoholate. Further, the presence of water is deleterious to the proper course of that reaction.

U.S. Pat. No. 6,015,440, for example, discloses that the glycerol from a biodiesel production unit functioning by homogeneous catalysis should be neutralized by strong cationic resins prior to the step for etherification by isobutene.

The crude glycerol obtained from conventional biodiesel production processes also cannot be used to be chemically modified by an aldehyde or ketone to produce an acetal as that reaction requires a neutral glycerol which is thus free of alcoholate. Further, the presence of water is deleterious to the proper course of the reaction.

If the glycerol containing catalyst or compounds derived from the catalyst is neutralized by an acid such as hydrochloric acid or sulphuric acid, for example, the neutral glycerol will contain salts such as sodium or potassium chlorides or sodium or potassium sulphates. In this case, a treatment to eliminate them has to be interposed between this step and the final step of incorporating the glycerol ether derivative or the glycerol acetal derivative into the fuel. This treatment generally consists of distilling the prepared product, which is expensive both as regards equipment and energy.

There exists a means of obtaining a neutral glycerol which is free of salt or water. It consists of using a heterogeneous catalyst, for example using the process described in FR-B-2 752 242.

Thus, the invention provides a process for producing a composition for use as a fuel or as a constituent of a fuel from at least one triglyceride formed between at least one fatty acid and glycerol, said process comprising:
  at least one transesterification step in which said triglyceride is reacted by heterogeneous catalysis with at least one primary monoalcohol selected from methanol and ethanol to produce at least one methyl and/or ethyl ester of the starting fatty acids of the triglycerides and glycerol, said products being free of by-products; and
  an etherification step in which the glycerol is reacted with at least one olefinic hydrocarbon containing 4 to 12 carbon atoms; and/or
  an acetalization step in which the glycerol is reacted with at least one compound selected from aldehydes, ketones and acetals derived from aldehydes or ketones.

Two types of catalysis can be envisaged to carry out the transesterification of a vegetable oil into methyl (or ethyl) esters from heterogeneous catalysts: a batch reactor catalyst or a continuous catalysis using the fixed bed principle. Generally, continuous fixed bed catalysis is employed.

In the transesterification step of the process of the invention, it is possible to use any solid catalyst functioning in heterogeneous mode, in particular selected from:
  those comprising at least one oxide of at least one element selected from groups IIB (for example Zn), IVA (for example Ti or Zr) and VB (for example Sb or Bi) of the periodic table;

those which comprise a mixture of at least aluminium oxide with at least one other oxide of at least one element selected from groups IIB, IVA and VB; and those which comprise at least one mixed oxide formed between aluminium oxide and at least one other oxide of at least one element selected from groups IIB, IVA and VB.

Hence, more particularly, the catalyst may comprise:

a mixture of zinc oxide and alumina or a zinc aluminate, for example of the spinel type, having the following formula:

$$ZnAl_2O_{4,x1}ZnO, y1Al_2O_3$$

(x1 and y1 each being in the range 0 to 2);

titanium oxide or a mixture of titanium oxide and alumina having the following formula:

$$(TiO_{x2})_{y2}(Al_2O_3)_{1-y2}$$

(x2 having a value of 1.5 to 2.2 and y2, representing the weight ratio of the two oxides, having a value of 0.005 to 1);

zirconium oxide or a mixture of zirconium oxide and alumina having the following formula:

$$(ZrO_{x2})_{y2}(Al_2O_3)_{1-y2}$$

(x2 having a value of 1.5 to 2.2 and y2, representing the weight ratio of the two oxides, having a value of 0.005 to 1);

a mixture of antimony oxide and alumina having the following formula:

$$(SbO_{x3})_{y3}(Al_2O_3)_{1-y3}$$

(x3 having a value of 1.2 to 2.6 and y3, representing the weight ratio of the two oxides, having a value of 0.005 to 0.995);

a mixture of zinc oxides and titanium or a mixture of zinc oxide, titanium oxide and alumina having the following formula:

$$[(ZnO)_a—(TiO_2)_b]_{y4}[Al_2O_3]_{1-y4}$$

this formula possibly also taking the form:

$$[Zn_aTi_bO_{(a+2b)}]_{y4}[Al_2O_3]_{1-y4}$$

(a having a value in the range 0.5 to 5, b having a value in the range 0.5 to 5 and y4 having a value of 0.005 to 1); or a mixture of oxides of bismuth and titanium or a mixture of bismuth oxide, titanium oxide and alumina having the following formula:

$$[(Bi_2O_3)_a—(TiO_2)_b]_{y4}[Al_2O_3]_{1-y4}$$

(a having a value in the range 0.5 to 5, b having a value in the range 0.5 to 5 and y4 having a value of 0.005 to 1).

As an example, the catalyst may be present in the form of extrudates with a diameter in the range 0.5 to 3 mm and is packaged in a tube allowing it to function in fixed bed mode. The diameter of the reactor must be adapted to the desired hourly production rate, and the whole reactor must be heated and pressure resistant. With this type of catalyst, it is possible, for example, to operate in the following manner, in one or more steps. An illustration is the case of preparing methyl esters.

Vegetable oil and methanol are introduced as an upflow into a reactor preheated to a temperature which may be in the range 170° C. to 250° C., preferably in the range 190° C. to 210° C., at operating pressures in the range 3 to 6 MPa with an HSV (volume of oil/volume of catalyst/hour) of 0.3/1 to 3/1 and preferably 0.4/1 to 2/1, and with a ratio by weight of alcohol/oil of 2/1 to 0.1/1. At the outlet from said reactor, excess methanol is partially eliminated by depressurization, which allows the glycerol formed to be eliminated by simple static decantation. The conversion of methyl esters obtained is, for example, in the range 85% to 97%.

If desired, the reaction may be continued in a second reactor. The second catalysis step is then carried out in the same operating condition ranges as described above, which can produce a high conversion of methyl esters, for example 97.5% to 99.5%. These latter then satisfy the required specifications for fuel esters. At the outlet from said second reactor, the excess methanol is completely eliminated by distillation and a second fraction of glycerol is obtained by decanting. It is mixed with the glycerol from the first step and this mixture is treated in a distillation apparatus to completely free it of the methanol.

This operation may also be continued at a temperature of 100° C. to 200° C., preferably 140° C. to 160° C. and at a pressure from atmospheric pressure to 5 mm Hg, preferably 15 to 5 mm Hg, to eliminate the compounds of the glycerol methyl ether family present to a lower limit of 0.6% by weight, for example.

If 210° C. is not exceeded during the catalysis step (or steps), an ester is generally obtained which has the same colour as the starting oil, along with a colourless glycerol.

In this case, the catalyst is not found either in the ester or in the glycerol. No neutralization or washing operation is required to eliminate the catalyst or a compound derived from the catalyst. The glycerol obtained is at least 98% pure. It contains no metals, no neutralization salts and its water content is limited by that of the starting products used during the biodiesel production, i.e. the oil and the mono-alcohol.

The glycerol obtained may be used directly in an etherification reaction with isobutene in the presence of an acid catalyst using a technique which is well known to the skilled person, with no prior treatment of glycerol. This reaction is, for example, described in U.S. Pat. No. 1,968,033.

It should be noted that during etherification, the composition of the mixture obtained may be changed either by modifying the glycerol/olefin ratio (for example isobutene), or by adjusting the residence time of the mixture on the catalyst.

The hydrocarbon-soluble glycerol derivative obtained (glycerol ether) may be incorporated into a gas oil, biodiesel or gasoline type fuel.

The glycerol ethers may be introduced into diesel fuels at a concentration at which they are soluble in said fuels. In these cases, proportions of 1% to 40% by volume are used, usually 1% to 20% by volume. The concentration of glycerol ethers in the gasoline may, for example, be up to 50% by volume.

In the example in which the glycerol derivative is a mixture of tertiobutyl ethers of glycerol, the process of the invention may be represented by the following reaction scheme:

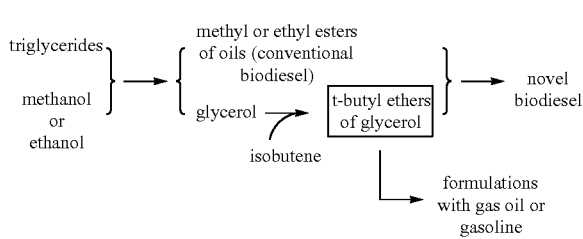

The novel biodiesel thus obtained may be used pure or as a mixture in gas oil and the mixture of tertiobutyl ethers of glycerol obtained may be incorporated into a gas oil alone or into a gas oil already containing biodiesel, or into a gasoline type fuel.

In this reaction scheme, all of the initial triglyceride is used as a fuel.

If, for example, all of the glycerol obtained by transesterification of a rapeseed oil by methanol is etherified by isobutene to obtain a mixture of mono-, di- and tri-tertiobutyl ethers the mean composition of which is equivalent to a di-tertiobutyl ether and if all of this mixture of ethers is incorporated into all of the methyl ester of the rapeseed oil obtained, a novel biodiesel is obtained the composition of which is close to 82% by weight of the methyl ester of the rapeseed oil and 18% by weight of a mixture of tertiobutyl ethers of glycerol. This novel biodiesel may be used as is in a diesel engine or mixed in any proportions with gas oil and/or a conventional biodiesel fuel. In this reaction scheme, all of the initial triglyceride is used as a fuel.

The glycerol ethers obtained by the production process of the invention may also have other applications, for example as solvents, surfactants or co-surfactants.

The glycerol obtained at the end of the transesterification step or steps may also be used directly in an acetalization reaction with an aldehyde or a ketone or an acetal derived from said aldehyde or from said ketone, in the presence of an acid catalyst using a technique which is well known to the skilled person and without prior treatment of said glycerol.

The acetalization reactions are, for example, described in the following documents:

J Gelas: Bulletin Soc Chimique de France, 1969, no 4, 1300;

J Gelas: Bulletin Soc Chimique de France, 1970, no 6, 2341;

A J Shower et al: Chem Rev, 1967, vol 67, 427;

Piantadosi et al: J of Am Chem Soc, 1958, vol 80, 6613.

The hydrocarbon-soluble glycerol derivative obtained (glycerol acetal) may be incorporated into a gas oil, biodiesel or gasoline type fuel.

Thus, the glycerol acetals may be introduced into the diesel fuels at a concentration at which they are soluble in said fuels. Depending on the case, proportions of 1% to 40% by volume, usually 1% to 20% by volume, are used.

The process of the invention may be represented by the following reaction scheme:

tion of which would be close to 87.5% by weight of the rapeseed oil methyl ester and 12.5% by weight of the solketal. This novel biodiesel could be used as is in a diesel engine or a mixture in all proportions with a gas oil and/or a conventional biodiesel fuel ester.

The glycerol acetals obtained by a production process of the invention may also have other applications, for example as solvents, surfactants or co-surfactants.

The following examples illustrate the invention without in any way limiting its scope.

EXAMPLE 1

A rapeseed oil was transesterified by methanol using a process employing a heterogeneous catalyst constituted by zinc aluminate.

In a fixed bed reactor heated to 200° C. and containing 70 ml of extrudates constituted by zinc aluminate, dosing pumps were used to introduce, as an upflow, 35 ml of rapeseed oil and 40 ml of absolute methanol per hour. The pressure in the apparatus was kept at 5 to 6 MPa. The reaction mixture was then evaporated so that the majority of the glycerol formed was eliminated by decanting.

The supernatant fraction of the esters produced containing about 94% by weight of methyl esters underwent a second catalysis step under identical operating conditions. The product resulting from said second catalysis step was completely freed of the excess methanol it contained by a distillation step. A second minor fraction of glycerol was obtained by decanting and was mixed with that obtained from the first catalysis step.

The glycerol was then vacuum treated to eliminate traces of methanol.

The glycerol obtained was intended for use without complementary treatment in the examples below.

EXAMPLES 2 TO 4

Synthesis of glycerol tertiobutyl ethers

Glycerol obtained from Example 1 was introduced in its crude form—i.e. with neither purification nor additional

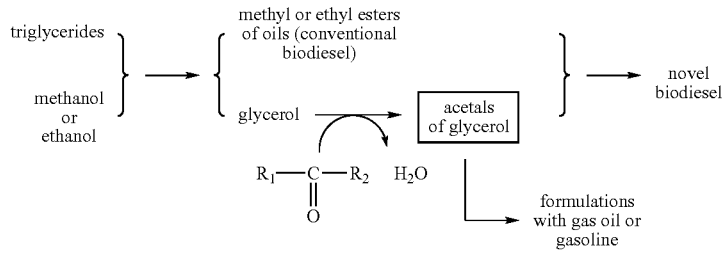

The novel biodiesel obtained may be used pure or as a mixture in gas oil and the glycerol acetal obtained may be incorporated into a gas oil alone or into a gas oil already containing biodiesel, or into a gasoline type fuel.

In this scheme as well, all of the initial triglyceride is used as a fuel.

If, for example, all of the glycerol obtained by transesterification of a rapeseed oil by methanol were to be acetalized by acetone to obtain 2,2-dimethyl-1,3-dioxolane-4-methanol, also sometimes termed solketal, and if all of that acetal were to be incorporated into all of the rapeseed oil methyl ester obtained, a novel biodiesel would be obtained the compositreatment—into an autoclave reactor equipped with an agitation system and a system for introducing a gas, containing a catalyst constituted by an acid type ion exchange resin, Amberlyst 15®. The medium was heated with stirring to a temperature of 50° C., then a controlled quantity of isobutene was introduced into the reactor. The temperature was maintained between 50° C. and 90° C. for 3 hours. After cooling to ambient temperature, the excess isobutene was purged, the catalyst was separated by filtering and any volatile components which may have been present were eliminated by evaporation. A colourless liquid was obtained which was a mixture of glycerol tertiobutyl ethers.

| | Etherification reaction | | Products obtained | | | Solubility of |
|---|---|---|---|---|---|---|
| | | | Mean composition | | | |
| Ex | Isobutene/glycerol Moles/mole | Amberlyst15/glycerol (g/kg) | Mono-t-Bu ethers (%) | di-t-Bu ethers (%) | Tri-t-Bu ethers (%) | biodiesel/ether mixture 80/20 |
| 2 | 2.05 | 5 | 39 | 50 | 8 | Yes |
| 3 | 2.5 | 5 | 26 | 59 | 14 | Yes |
| 4 | 2.8 | 5 | 20 | 63 | 16 | Yes |

EXAMPLE 5

Glycerol obtained in accordance with Example 1 and isobutene in a molar ratio of 1:2.8 were introduced into a fixed bed reactor containing 50 ml of washed and dried Amberlyst 15® resin, maintaining a flow rate which ensured a residence time of 30 minutes at a temperature of 80° C. and a pressure of 1 MPa.

As appropriate, at the reactor outlet, the excess isobutene was eliminated by depressurization and, after evaporating off any isobutene oligomers, a product was obtained the composition of which was analogous to that of the mixture obtained in Example 4 (see Table 1 above).

EXAMPLE 6

920 g (10 moles) of glycerol obtained as described in Example 1, 790.3 g (10.96 moles) of n-butyraldehyde and 24 g of an Amberlyst 15® acid resin were introduced into a reactor. The medium was heated to 54° C. with stirring for 7 hours during which 120 g of n-butyraldehyde was introduced.

The reaction was as follows:

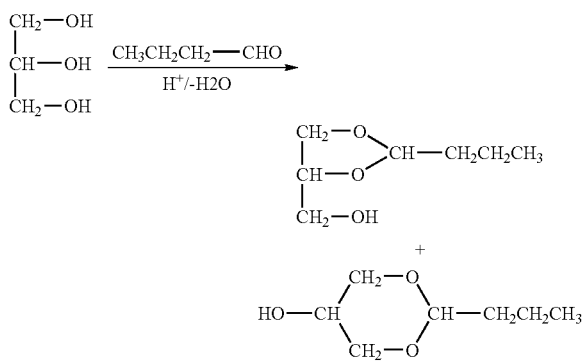

The product generally exists in the two isomeric forms represented above.

After cooling to ambient temperature, the catalyst was eliminated by filtration, then the excess n-butyraldehyde and the water of reaction were eliminated by evaporation under reduced pressure. 1165 g of a clear biodiesel-soluble liquid was recovered in a proportion of 80/20 biodiesel/acetal with the following elemental analysis:

C=56.7% by weight;
H=10.1% by weight;
O=33.2% by weight.

EXAMPLE 7

The preceding example was repeated, replacing the n-butyraldehyde by an equimolar quantity of acetone and operating at a temperature in the range 50° C. to 80° C.

The reaction was as follows:

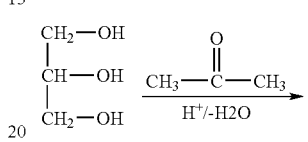

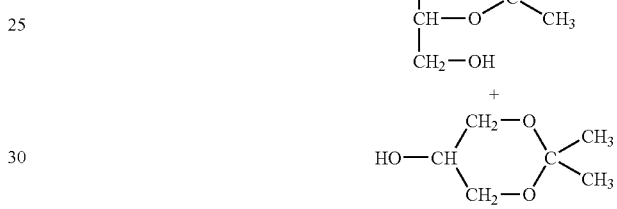

A clear biodiesel-soluble liquid was recovered in a proportion of 87/13 biodiesel/acetal with the following elemental analysis:

C=54.5% by weight;
H=9.1% by weight;
O=36.4% by weight.

EXAMPLE 8

A fixed bed reactor containing 50 cm$^3$ of an Amberlyst 15® resin was supplied with glycerol obtained as described in Example 1 and acetone in an acetone/glycerol molar ratio of 1.2:1. The flow rate of the two reagents was adjusted so that the residence time was 30 minutes. The temperature in the reactor was raised to and maintained at 80° C. and the pressure was maintained at 5 bars (0.5 MPa). At the reactor outlet, the medium underwent depressurization then the residual acetone and water from the reaction were eliminated by evaporation under reduced pressure.

The recovered liquid product was introduced into a second fixed bed reactor which was identical to the first, also supplied with acetone in an acetone/effluent weight ratio of the first reactor of 50/100. The reaction in said second reactor was carried out under the same conditions as those described for the first. At the outlet from the second reactor, the medium underwent depressurization then the residual acetone and water from the reaction were eliminated by evaporation under reduced pressure.

The recovered liquid product had the same characteristics as that obtained in Example 7.

The invention claimed is:

1. A process for producing two families of biofuels from at least one triglyceride, formed between at least one fatty acid and glycerol, characterized in that it comprises:
a reaction of at least one transesterification step in which said triglyceride is reacted by heterogeneous catalysis with at least one primary monoalcohol selected from methanol and ethanol to produce a mixture of at least one methyl and/or ethyl ester of the fatty acids of the starting triglyceride(s) as first biofuel, and glycerol, separating heterogeneous catalyst from said mixture, wherein the heterogeneous catalyst comprises any of
a mixture of titanium oxide and alumina having the following formula:

$(TiO_{x2})_{y2}(Al_2O_3)_{1-y2}$ x2 having a value of 1.5 to 2.2 and y2, representing the weight ratio of the two oxides, having a value of 0.0005 to 1;
a mixture of antimony oxide and alumina having the following formula:

$(SbO_{x3})_{y3}(Al_2O_3)_{1-y3}$ x3 having a value of 1.2 to 2.6 and y3, representing the weight ratio of the two oxides, having a value of 0.005 to 0.995;
a mixture of zinc oxide, titanium oxide and alumina having the following formula:

$[(ZnO)_a-(TiO_2)_b]_{y4}[Al_2O_3]_{1-y4}$ a having a value in the range 0.5 to 5, b having a value in the range 0.5 to 5 and y4 having a value of 0.0005 to 1: or
a mixture of oxides of bismuth and titanium or a mixture of bismuth oxide, titanium oxide and alumina having the following formula:

$[(Bi_2O_3)_a-(TiO_2)_b]_{y4}[Al_2O_3]_{1-y4}$ a having a value in the range 0.5 to 5, b having a value in the range 0.5 to 5 and y4 having a value of 0.005 to 1,
separating the crude glycerol from resultant mixture and subjecting the crude glycerol to a vacuum treatment to remove said at least one primary monoalcohol; and
an etherification step in which the resultant vacuum treated crude glycerol is reacted directly with at least one olefinic hydrocarbon containing 4 to 12 carbon atoms to obtain at least one glycerol ether as the second biofuel; and/or
an acetalization step in which the resultant vacuum treated crude glycerol is reacted directly with at least one compound selected from aldehydes, ketones and acetals derived from aldehydes or ketones, to obtain at least one glycerol acetal as the second biofuel, and directly adding the resultant etherified and/or acetalized crude vacuum treated glycerol to a fuel comprising said first biofuel.

2. A process according to claim 1, characterized in that:
vegetable oil and methanol are introduced as continuously upflow into a fixed bed catalytic transesterification reactor preheated to a temperature which in the range of 170° to 210° C. at an operating temperature in the range 3 to 6 MPa, with an HSV (volume of oil/volume of catalyst/hour) of 0.3/1 to 3/1 and an alcohol/oil weight ratio of 2/1 to 0.1/1; and
at the reactor outlet, depressurizing to at least partially eliminate the excess methanol and the glycerol formed is eliminated by simple static decantation;
the conversion of the methyl esters obtained being in the range 85% to 97%.

3. A process according to claim 1, comprising an acetalization step carried out between the glycerol obtained from the transesterification step directly without neutralization or washing steps and an aldehyde, a ketone or an acetal derived from said aldehyde or said ketone in the presence of an acid catalyst.

4. A process according to claim 1, comprising
an acetalization step in which the glycerol from the transesterification step is reacted directly, without prior neutralization or washing treatments, with at least one compound selected from aldehydes, ketones an acetals derived from aldehydes or ketones, to obtain at least one glycerol acetal; and
incorporating the glycerol acetal obtained into a fuel.

5. A process according to claim 4, wherein said at least one triglyceride is rapeseed oil and wherein the glycerol is acetalized with acetone to form 2,2-dimethyl-1,3-dioxolane-4-methanol.

6. A process according to claim 1, wherein said catalyst comprises
said mixture of oxides of bismuth and titanium or a mixture of bismuth oxide, titanium oxide and alumina having the following formula:

$[(Bi_2O_3)_a-(TiO_2)_b]_{y4}[Al_2O_3]_{1-y4}$ a having a value in the range 0.5 to 5, b having a value in the range 0.5 to 5 and y4 having a value of 0.005 to 1.

7. A process according to claim 1, wherein said catalyst comprises a mixture of titanium oxide in alumina having a following formula $(TiO_{x2})_{y2}(Al_2O_3)_{1-y2}$ x2 having a value of 1.5 to 2.2 and y2, representing the weight ratio of the two oxides, having a value of 0.0005 to 1.

8. A process according to claim 1, wherein the catalyst is a mixture of antimony oxide and alumina having a following formula $(SbO_{x3})_{y3}(Al_2O_3)_{1-y3}$ x3 having a value of 1.2 to 2.6 and y3, representing the weight ratio of the two oxides, having a value of 0.005 to 0.995.

9. A process according to claim 1, wherein the catalyst is a mixture of zinc oxide, titanium oxide and alumina having a following formula $[(ZnO)_a-(TiO_2)_b]_{y4}[Al_2O_3]_{1-y4}$ a having a value in the range 0.5 to 5, b having a value in the range 0.5 to 5 and y4 having a value of 0.0005 to 1.

10. A process according to claim 1, wherein said reaction 1 is conducted in a reactor and said reactor contains a reaction mixture consisting of reactants, catalysts and products.

11. A process according to claim 1, wherein the triglyceride is rapeseed oil and the monoalcohol is methanol and wherein the etherification step is conducted in the presence of an acid catalyst between isobutene and the glycerol from the transesterification step.

12. A process for producing two families of biofuels from at least one triglyceride, formed between at least one fatty acid and glycerol, characterized in that it comprises:
a reaction of at least one transesterification step in which said triglyceride is reacted by heterogeneous catalysis with at least one primary monoalcohol selected from methanol and ethanol to produce a mixture of at least one methyl and/or ethyl ester of the fatty acids of the starting triglyceride(s) as first biofuel, and glycerol, separating heterogeneous catalyst from said mixture, wherein the heterogeneous catalyst comprises any of a mixture of titanium oxide and alumina having the following formula:

$$(TiO_{x2})_{y2}(Al_2O_3)_{1-y2}$$

x2 having a value of 1.5 to 2.2 and y2, representing the weight ratio of the two oxides, having a value of 0.0005 to 1;

a mixture of antimony oxide and alumina having the following formula:

$$(SbO_{x3})_{y3}(Al_2O_3)_{1-y3}$$

x3 having a value of 1.2 to 2.6 and y3, representing the weight ratio of the two oxides, having a value of 0.005 to 0/995;

a mixture of zinc oxide, titanium oxide and alumina having the following formula:

$$[(ZnO)_a\text{—}(TiO_2)_b]_{y4}[Al_2O_3]_{1-y4}$$

a having a value in the range 0.5 to 5, b having a value in the range 0.5 to 5 and y4 having a value of 0.0005 to 1: or a mixture of oxides of bismuth and titanium or a mixture of bismuth oxide, titanium oxide and alumina having the following formula:

$$[(Bi_2O_3)_a\text{—}(TiO_2)_b]_{y4}[Al_2O_3]_{1-y4}$$

a having a value in the range 0.5 to 5, b having a value in the range 0.5 to 5 and y4 having a value of 0.005 to 1, separating the crude glycerol from resultant mixture and subjecting the crude glycerol to a vacuum treatment to remove said at least one primary monoalcohol; and an etherification step in which the resultant vacuum treated crude glycerol from the transesterification step is reacted directly with at least one olefinic hydrocarbon containing 4 to 12 carbon atoms to obtain at least one glycerol acetal as the second biofuel; and/or an acetalization step in which the resultant vacuum treated crude glycerol from the transesterification step is reacted directly with at least one compound selected from aldehydes, ketones and acetals derived from aldehydes or ketones, to obtain at least one glycerol acetal as the second biofuel, and directly adding the resultant etherified and/or acetalized crude vacuum treated glycerol to a fuel comprising all of said first biofuel characterized in that the reaction I is continued in a second catalysis step in a second reactor having an inlet and an outlet carried out under the same operating conditions as in the first catalysis step, to achieve a methyl ester conversion of 97.5% to 99.5%, and at the outlet of the second reactor, excess methanol is removed by distillation to free the methyl ester of methanol.

13. A process according to claim 12, wherein said catalyst comprises a mixture of titanium oxide in alumina having a following formula $$(TiO_{x2})_{y2}(Al_2O_3)_{1-y2}$$

x2 having a value of 1.5 to 2.2 and y2, representing the weight ratio of the two oxides, having a value of 0.0005 to 1.

14. A process according to claim 12, wherein the catalyst is a mixture of antimony oxide and alumina having a following formula $$(SbO_{x3})_{y3}(Al_2O_3)_{1-y3}$$

x3 having a value of 1.2 to 2.6 and y3, representing the weight ratio of the two oxides, having a value of 0.005 to 0.995.

15. A process according to claim 12, wherein the catalyst is a mixture of zinc oxide, titanium oxide and alumina titanium having a following formula $$[(ZnO)_a\text{—}(TiO_2)_b]_{y4}[Al_2O_3]_{1-y4}$$

a having a value in the range 0.5 to 5, b having a value in the range 0.5 to 5 and y4 having a value of 0.0005 to 1.

16. A process according to claim 12, wherein said catalyst comprises a mixture of oxides of bismuth and titanium or a mixture of bismuth oxide, titanium oxide and alumina having the following formula:

$$[(Bi_2O_3)_a\text{—}(TiO_2)_b]_{y4}[Al_2O_3]_{1-y4}$$

a having a value in the range 0.5 to 5, b having a value in the range 0.5 to 5 and y4 having a value of 0.005 to 1.

17. A process according to claim 12, wherein said transesterification step is conducted in a reactor containing a reaction mixture consisting of reactants, catalysts and products.

* * * * *